United States Patent
Pidria et al.

(10) Patent No.: US 7,350,397 B2
(45) Date of Patent: Apr. 1, 2008

(54) DEVICE FOR MEASURING THE QUANTITY OF SOLID PARTICLES IN A GAS MEDIUM

(75) Inventors: Marco Federico Pidria, Orbassano (IT); Valentina Grasso, Orbassano (IT); Paolo Faraldi, Orbassano (IT); Vito Lambertini, Orbassano (IT)

(73) Assignee: C.R.F. Societa Consortile per Azioni, Orbassano (Torino) (IT)

( * ) Notice: Subject to any disclaimer, the term of this patent is extended or adjusted under 35 U.S.C. 154(b) by 509 days.

(21) Appl. No.: 11/040,105

(22) Filed: Jan. 24, 2005

(65) Prior Publication Data

US 2005/0180888 A1 Aug. 18, 2005

(30) Foreign Application Priority Data

Feb. 6, 2004 (EP) ................... 04425076

(51) Int. Cl.
*G01N 7/08* (2006.01)
(52) U.S. Cl. ................. 73/23.33
(58) Field of Classification Search .............. 73/23.33, 73/28.01, 31.05; 324/691
See application file for complete search history.

(56) References Cited

U.S. PATENT DOCUMENTS

| | | | | |
|---|---|---|---|---|
| 4,979,364 | A * | 12/1990 | Fleck | 60/274 |
| 5,008,628 | A * | 4/1991 | Krigmont et al. | 324/693 |
| 5,247,827 | A * | 9/1993 | Shah | 73/28.01 |
| 5,581,091 | A * | 12/1996 | Moskovits et al. | 257/9 |
| 5,756,879 | A * | 5/1998 | Yamagishi et al. | 73/28.01 |
| 6,359,288 | B1 * | 3/2002 | Ying et al. | 257/14 |
| 6,705,152 | B2 * | 3/2004 | Routkevitch et al. | 73/31.05 |
| 6,709,929 | B2 * | 3/2004 | Zhang et al. | 438/268 |
| 6,914,256 | B2 * | 7/2005 | Zhang et al. | 257/15 |
| 6,938,409 | B2 * | 9/2005 | Birckigt et al. | 60/275 |
| 6,946,197 | B2 * | 9/2005 | Yadav et al. | 428/402 |
| 6,952,055 | B2 * | 10/2005 | Scherer et al. | 257/798 |
| 7,189,471 | B2 * | 3/2007 | Jankowksi et al. | 429/38 |
| 2001/0035044 | A1 * | 11/2001 | Larsson et al. | 73/28.01 |
| 2002/0118027 | A1 * | 8/2002 | Routkevitch et al. | 324/694 |
| 2003/0039874 | A1 * | 2/2003 | Jankowski et al. | 429/26 |
| 2006/0097633 | A1 * | 5/2006 | Cho et al. | 313/512 |
| 2007/0039858 | A1 * | 2/2007 | Noca et al. | 210/94 |

FOREIGN PATENT DOCUMENTS

JP 60174940 A * 9/1985

OTHER PUBLICATIONS

Routkevitch et al, "Nonlithographic Nano-Wire Arrays: Fabrication, Physics, and Device Applications", IEEE Transactions on Electron Devices, vol. 43, No. 10, Oct. 1996, pp. 1646-1658.

* cited by examiner

*Primary Examiner*—Hezron Williams
*Assistant Examiner*—John Fitzgerald
(74) *Attorney, Agent, or Firm*—Nixon & Vanderhye P.C.

(57) ABSTRACT

A device for detecting the amount or concentration of particulate matter in a gas medium comprises a structure for the deposit of solid particles, at least a first and a second electrode associated to the structure, and means for measuring an electric quantity between the first and second electrode. A plurality of cavities is defined in the structure, which act as collectors of solid particles, the structure being arranged so as to induce the accumulation of the particles inside the cavities.

20 Claims, 3 Drawing Sheets

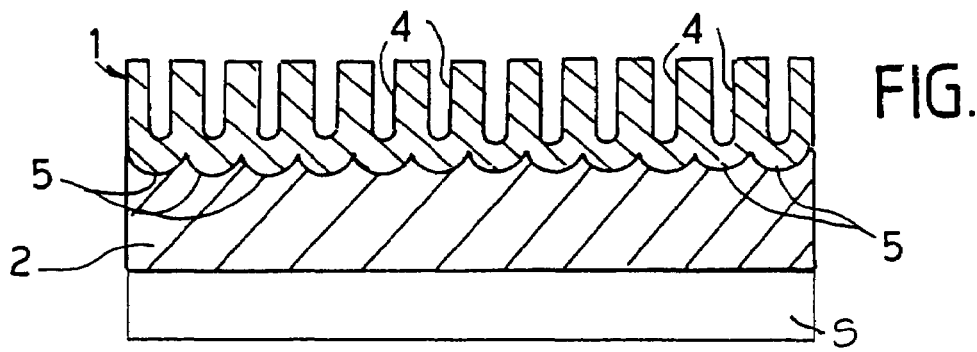
FIG. 5
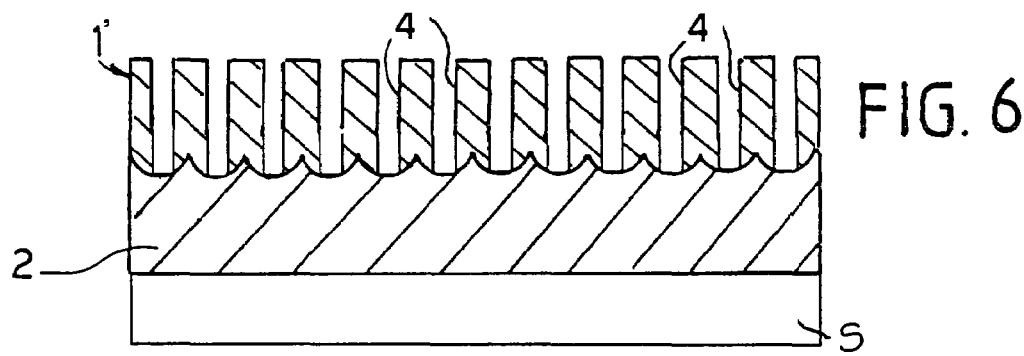
FIG. 6
FIG. 7
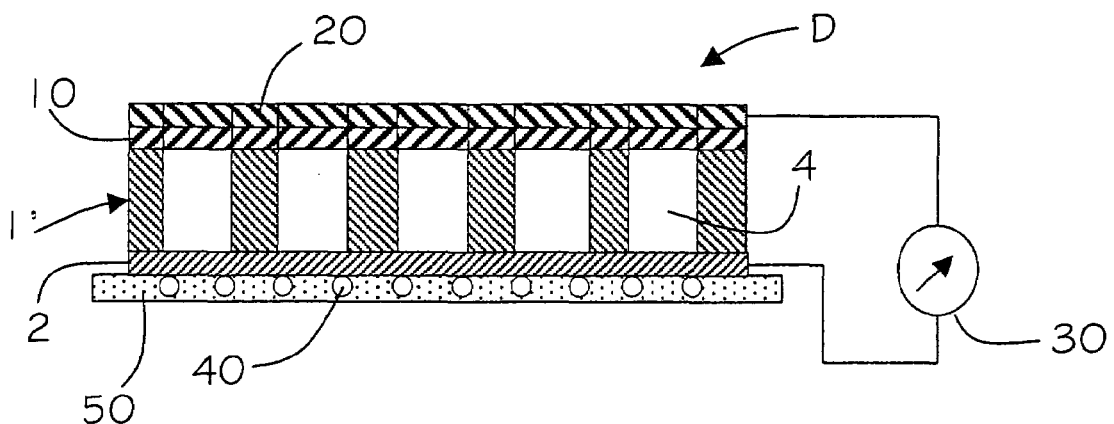

DEVICE FOR MEASURING THE QUANTITY OF SOLID PARTICLES IN A GAS MEDIUM

FIELD OF THE INVENTION

The present invention relates to a device for the cumulative measure of the amount of solid particles in a gas medium.

DESCRIPTION OF THE PRIOR ART

Devices as referred to above are for instance used for detecting the level of carbon particulate matter in exhaust gases of vehicles with internal combustion engines.

Known detecting devices include those comprising a flat supporting structure, made of insulating material, to one of whose surfaces at least two electrodes with interdigitized conductive tracks are associated, as well as means designed to measure variations of electrical resistance between said electrodes. The supporting structure is arranged inside the exhaust conduit of the vehicle engine, so that part of the particulate matter in exhaust gases can deposit onto said flat surface. Particulate matter is basically a conductive compound based on carbon and its particles, depositing onto the flat surface of the device, tend to form conductive bridges between the interdigitized tracks of the electrodes, which results in a progressive decrease of electric resistance at the ends of the latter. Thanks to the variation of electrical resistance with respect to an initial value it is possible to calculate in an integral way the amount of particulate matter in exhaust gases.

Known devices as referred to above do not enable to carry out sufficiently accurate detections, for instance for engine control or to diagnostic purposes, since the variation of electrical resistance is strongly non-linear being subject to an "avalanche" phenomenon.

This phenomenon is basically due to the distribution with fractal structure of particulate matter on sensor surface; said structure has a critical interconnection threshold, above which the value of electrical resistance sinks dramatically.

SUMMARY OF THE INVENTION

In the light of the above, the present invention aims at carrying out a new device for detecting the amount of solid particles in a gas medium, having in particular a linear, repeatable characteristic curve.

Said aim is achieved according to the present invention by a device for detecting the amount or concentration of solid particles of nanometric or sub-micrometric size in a gas medium, in particular particulate matter in the exhaust gas of an internal combustion engine, comprising:

a structure for the deposit of solid particles present in the gas medium, at least a first and a second electrode associated to said structure, and means for measuring an electric quantity between the first and second electrode, characterized in that in said structure a plurality of cavities is defined, acting as collectors of solid particles in the gas medium, said structure being designed to enable the collection of said particles inside said cavities.

Preferred characteristics of the device according to the invention are listed in the appended claims, which are an integral and substantial part of the present description.

BRIEF DESCRIPTION OF THE DRAWINGS

Further aims, characteristics and advantages of the present invention shall be evident from the following detailed description and from the accompanying drawings, given as a mere illustrative and non-limiting example, in which:

FIG. 2-6 show consecutive steps of a process for making a porous film of aluminum oxide grown on a metal substrate, used in a detecting device according to the invention;

FIGS. 7 and 8 are partial, schematic views, a sectioned view and a perspective view respectively, of a device according to the invention;

DETAILED DESCRIPTION OF THE INVENTION

As explained above, detecting devices according to the prior art are basically characterized by a flat structure, defining a surface for particulate matter deposit, on which at least two electrodes are present. Conversely, the detecting device according to the present invention is characterized by the use of a porous matrix, whose cavities are designed to house solid particles of nanometric or sub-micrometric size present in the gas to be analyzed. As shall be seen, for instance, the progressive accumulation of carbon particles in the cavities thus obtained results in a progressive, regular variation of electric resistance.

In the preferred embodiment of the invention, the aforesaid matrix is made of porous aluminum oxide ($Al_2O_3$) obtained by means of an anodization process; said material, hereinafter referred to as alumina, has properties of electrical insulation, is resistant to high temperatures and has a highly regular porous structure.

The structure of porous alumina can be ideally schematized as a lattice or reticule of aligned pores, extending from the outer surface to the underlying metal layer. Porous alumina can be obtained by means of a particular process of anodization of highly pure aluminum sheets or of aluminum films deposited onto substrates such as glass, quartz, silicon, tungsten, etc.

Figure 1:
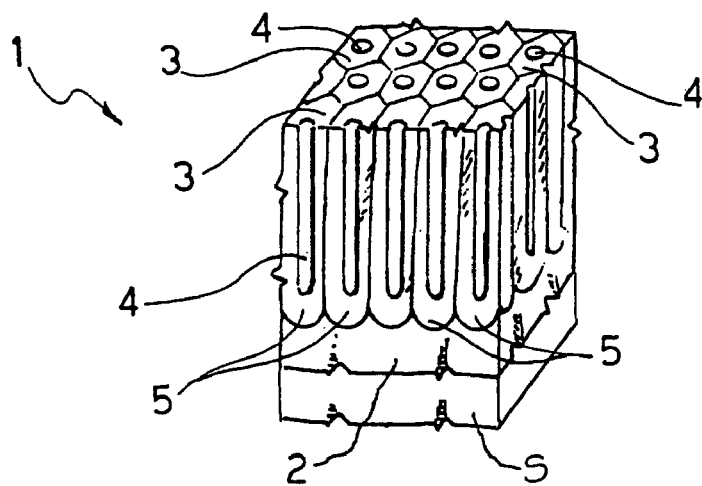
FIG. 1 is a schematic perspective view of a portion of a porous film of aluminum oxide (hereinafter referred to as alumina) grown on a metal substrate.

FIG. 1 shows as a mere example a portion of a porous alumina film, globally referred to with number 1, obtained by means of anodic oxidation of an aluminum layer 2 placed on a convenient substrate S. As can be observed, the alumina layer 1 consists of a series of typically hexagonal, directly adjacent cells 3, each having a central straight passage creating a pore 4, basically perpendicular to the surface of the aluminum layer 2. The end of each cell 3 on the aluminum layer 2 has a closing portion having a typically hemispheric shape, the whole of said closing portions making up a non-porous part of the film 1, or barrier layer, referred to with number 5.

The film 1 can be developed with controlled morphology by conveniently choosing the physical, chemical and electrochemical parameters of the process: in acid electrolytes (such as phosphoric acid, oxalic acid and sulfuric acid) and under suitable process conditions (voltage, current, stirring and temperature), highly regular porous films can be obtained. To this purpose, the size and density of the cells 3, the diameter of the pores 4 and the height of the film 1 can be varied; for instance the diameter of the pores 4, which is typically of 50-500 nm, can be controlled by chemical treatments. The pores of the alumina used in the application here suggested preferably have a diameter of 200-300 nm, so as to enable the entry and therefore the detection of sub-micrometric particulate matter.

Figure 2:
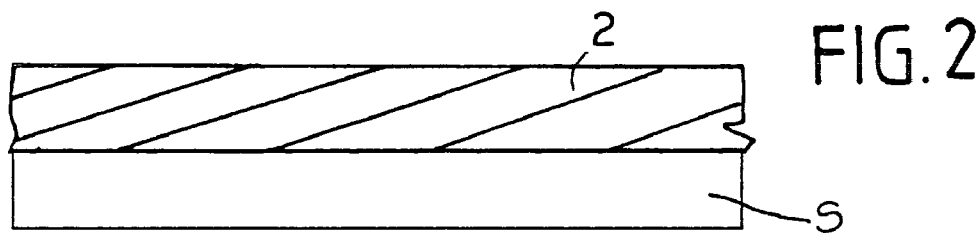

As schematized in FIG. 2, the first step in the manufacturing of the porous alumina film 1 is the deposition of the aluminum layer 2 onto a convenient substrate S, the latter being for instance made of silicon. This operation requires a deposit of highly pure materials with thicknesses of one μm to 50 μm. Preferred techniques for depositing the layer 2 are thermal evaporation via e-beam and sputtering.

The step including the deposition of the aluminum layer 2 is followed by an anodization step of said layer. The anodization process of the layer 2 can be carried out by using different electrolytic solutions depending on the desired size and distance of pores 4.

Should the electrolyte be the same, concentration, current density and temperature are the parameters that greater affect the size of pores 4. The configuration of the electrolytic cell is also important in order to obtain a correct distribution of the shape lines of the electric field with a corresponding uniformity of the anodic process.

Figure 3:
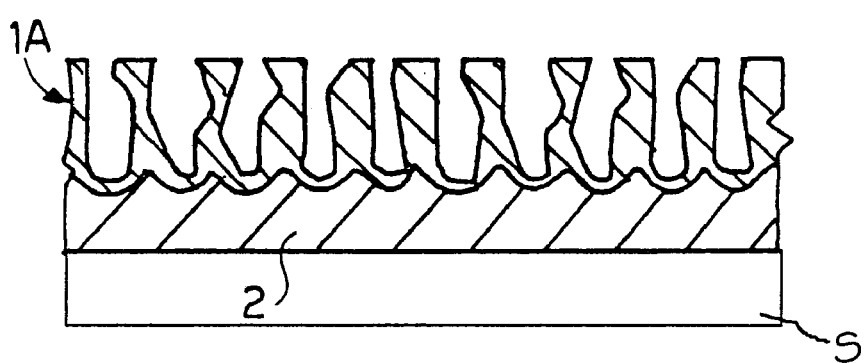
Figure 4:
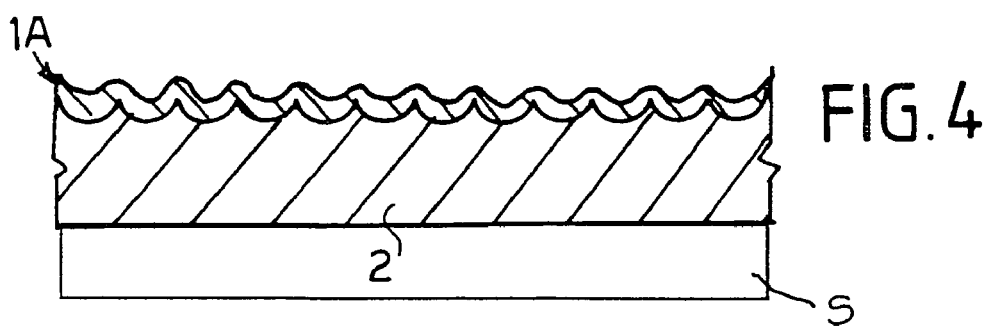

FIG. 3 schematically shows the result of the first anodization of the aluminum layer 2; as shown, the alumina film, here referred to with number 1A, obtained through the first anodization of the layer 2, does not have a regular structure. In order to obtain a highly regular structure, such as the one referred to with number 1 in FIG. 1, it is necessary to perform consecutive anodization processes, and in particular at least i) a first anodization, whose result is basically the one in FIG. 3;

ii) a reduction step through etching of the irregular alumina film 1A, performed by means of acid solutions (for instance $CrO_3$ and $H_3PO_4$); FIG. 4 schematically shows the situation after said etching step;

iii) a second anodization of the aluminum layer starting from the alumina film 1A that has not been removed through etching.

The etching step referred to in ii) is important in order to define on the residual alumina part 1A preferential areas for alumina growth in the second anodization step.

By performing several times the consecutive operations involving etching and anodization, the structure improves until it becomes highly uniform, as schematically shown in FIG. 5, where the alumina film 1 is now regular.

In the case of the present invention, after obtaining the regular porous alumina film 1, a step involving a total or local removal of the barrier layer 5 is carried out, so that the pores 4 take the shape of holes getting through the alumina structure. Indeed, the barrier layer 5 fully insulates the alumina structure: the reduction of said layer 5 is therefore fundamental so as both to perform consecutive electrodeposition processes, if necessary, requiring an electric contact, and to detect electric quantities, as shall be seen below.

The aforesaid process involving the removal or reduction of the barrier layer 5 can include two consecutive stages:

widening of pores 4, if necessary, performed in the same electrolyte as in previous anodization, without passage of current;

reduction of the barrier layer 5, performed by passage of very low current in the same electrolyte as in previous anodization; at this stage the typical balance of anodization is not achieved, thus favoring an etching process with respect to an alumina-building process.

FIG. 6 shows the result of the aforesaid process of removal of the barrier layer, as a result of which the pores 4 of the alumina film, now referred to with number 1', open directly also on the underlying aluminum layer 2, on which alumina has been grown, as previously described.

Figure 8:
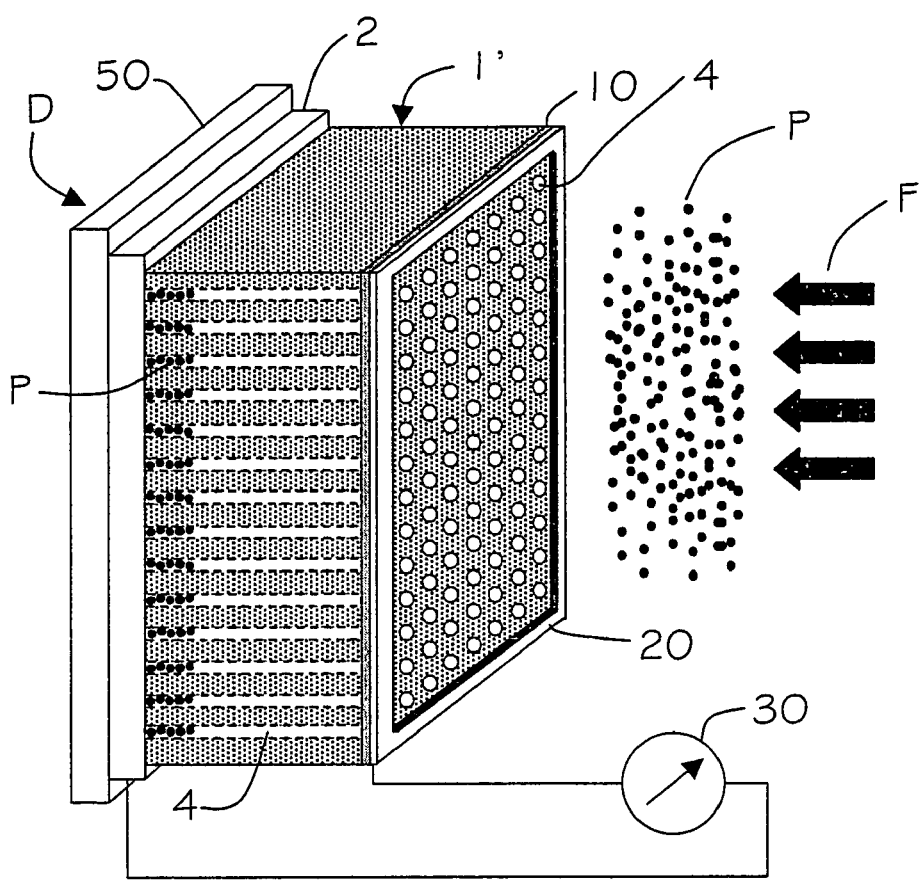

In order to carry out the detection device according to the invention, globally referred to with D in FIGS. 7 and 8, the following layers are deposited onto the film 1' starting from the side of the structure opposite the aluminum layer 2: a layer of insulating material and a layer of conductive material building an electrode, referred to with numbers 10 and 20, respectively. The insulating layer 10 and the electrode 20 can consist of an insulating paste and a conductive paste, respectively, deposited with screen printing techniques or by evaporation onto porous alumina 1'. The insulating layer 10 prevents possible short-circuits between the metal layer under alumina and the conductive layer 20.

It should be pointed out that the materials constituting the insulating layer 10 and the electrode 20 are deposited so as not to fill up and obstruct the pores 4, so that the latter can act as collectors of solid particles. In said light, the insulating layer 10 and the electrode 20 can be arranged as a grid on the porous surface of alumina 1'; FIG. 8 only shows the peripheral mesh of said grid, for higher clarity of representation.

The device D then comprises measuring means 30, known per se, designed to detect the variation of electric resistance, due to the collection of particulate matter in the pores 4, between the electrode 20 and the aluminum layer 2, which constitutes the second electrode of the device D.

FIG. 8 shows schematically the device D in a condition of possible use; to said purpose let us assume that the device D is arranged inside an exhaust tube of a vehicle with internal combustion engine.

The device D is mounted so that the open end of the pores 4, which overlooks the electrode 20, is opposed to the flow direction normally followed by exhaust gases, as schematically referred to with arrows F. As was said, particulate matter is present in gases F, which basically consists of sub-micrometric or nanometric particles based on conductive carbon. The aforesaid particles are shown schematically by the spots referred to with P in FIG. 8; as can be inferred from said figure, the arrangement is such that the flow F causes the entry of particles P into the pores 4 of the alumina film 1' of the device D.

The method followed for detecting the level of particulate matter includes, in a preliminary phase, the calculation of the resistive component of the impedance of the sensor device, which can be detected between the two electrodes, defined as variable resistance, since it depends on a series of parallel resistances due to the various layers 2, 1', 10, 20 making up the device D. Said resistive value is initially in the order of megaohms, since porous alumina—as was said—is a basically insulating material.

Then, when as a result of engine operation and thus of the emission of exhaust gases, particles deposit and accumulate progressively within the pores 4, a variation of resistance as measured through the means 30 can be observed. Practical tests have enabled to detect for instance, with the gas flow F containing particulate matter P, reductions of resistance value up to 40% with respect to the initial value without particles P inside the pores 4. Said analysis have further shown that the resistance value as measured varies proportionally to the concentration of particles P in the gas carrier F.

The detection of resistance variation, with the flow F, with respect to an initial value, performed through the measuring means 30, thus allows to carry out an integral "batch" or cumulative integral measuring of the level of particulate matter, according to known techniques (as was mentioned in the introduction to the present description, thanks to the variation of electrical resistance measured with respect to an initial value it is possible to calculate integrally the level of particulate matter in exhaust gases, by means of suitable transfer functions).

At the end of the above-described step of measuring of resistance variation, or when a given saturation of threshold of the device D is reached, the latter should be "regenerated", by removing the particulate matter P trapped in the pores 4.

This can be achieved by associating to the structure of the device D a heater, for instance a metal electric resistor, operative to heat the structure of said device and then burn the particulate matter P. Such a resistor, referred to with number 40 in FIG. 7, for instance shaped like a coil, can be advantageously integrated into a metal support 50 of the device D, so as to be close to the layer 2.

When the device D has to be regenerated, the resistor 40 is supplied with electric energy, so as to heat the structure of the device up to 630-650° C. i.e. to a temperature causing oxidation and therefore the removal of the particles P collected in the pores 4.

The device D, being a sensor for cumulative measuring of integral type, can be advantageously used for taking measurings in a particulate matter filter present in the exhaust conduit of motor vehicles with internal combustion engines, for instance diesel engines. The invention can obviously be used also in other fields than the automotive one, in order to measure the amount or concentration of particles in a generic gas medium.

The description disclosed above points out the features of the invention and its advantages with respect to the prior art, mainly consisting in that the particular morphology of the supporting material 1' of the sensor D allows to trap particulate matter, with the possibility of carring out its proportional measuring having transfer characteristics not effected by the "avalanche" effect typical of prior art.

Obviously, though the basic idea of the invention remains the same, construction details and embodiments can widely vary with respect to what has been described and shown by mere way of example.

Figure 9:
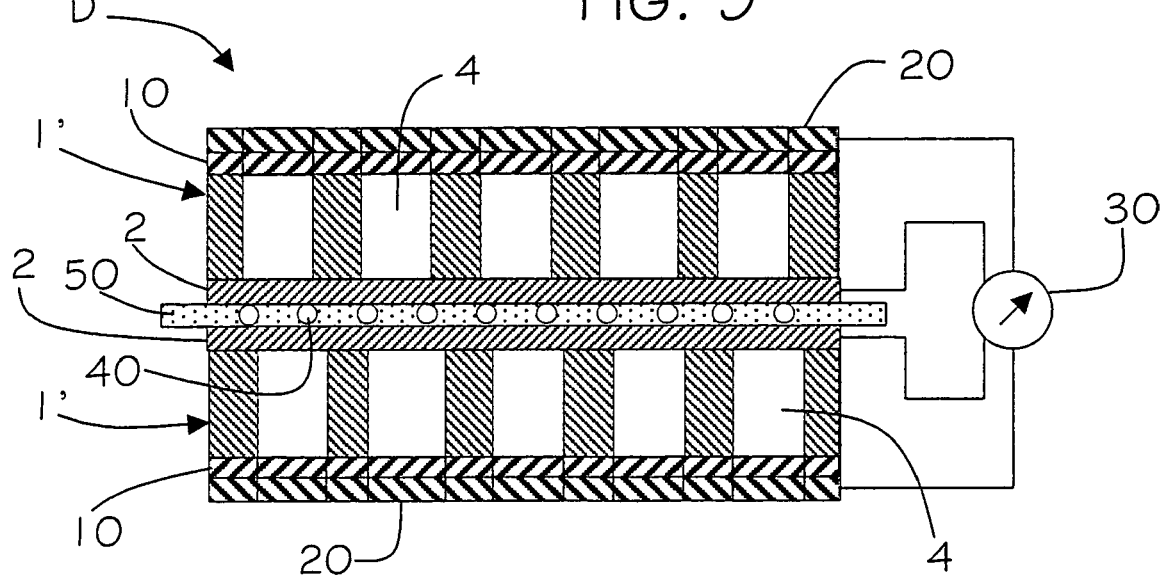
FIG. 9 is a partial, schematic section of a device carried out in accordance with a possible execution variant of the invention.

FIG. 9 shows by way of example a possible execution variant of the invention, according to which the sensor device D comprises two porous structures opposed one to the other with respect to the same support 50 integrating the resistor 40, each structure comprising its own layers 2, 1', 10, 20. Said structure, which improves the exploitation of a given sensitive area, preferably requires a housing having such fluid-dynamic features as to convey gases carrying particulate matter onto both surfaces of the sensor device D.

In the case described above, the level of solid particles in the gas medium is calculated on the basis of variations of electric resistance; however, it is obvious for the person skilled in the art that the detections performed by the sensor could be capacitive.

The electrode referred to above with number 2 should not necessarily be made of aluminum; in such a case the aluminum layer 2 on which alumina 1' has been grown can be removed through known etching techniques, so as to enable the direct contact of said structure with another conductive material acting as electrode of the device.

What is claimed is:

1. Device for detecting the amount or concentration of solid particles of nanometric or sub-micrometric size in a gas medium, in particular particulate matter in the exhaust gas of an internal combustion engine, comprising:
 a structure for the deposit of solid particles present in the gas medium,
 at least a first and a second electrode associated to said structure, and
 means for measuring an electric quantity between the first and second electrodes,
 wherein a plurality of cavities is defined in said structure, which act as collectors of solid particles present in the gas medium, the structure being arranged so as to enable collection of said particles inside said cavities, and
 wherein said structure comprises a porous body made of an electrically insulating material, the pores of said body constituting at least part of said cavities.

2. Device according to claim 1, wherein said porous body is made at least partly of anodized porous alumina.

3. Device according to claim 1, wherein a second end of said cavities is open towards said second electrode.

4. Device according to claim 1, wherein an end of said cavities is open so as to receive said particles, and is in particular opposed to the direction of a flow of the gas medium.

5. Device according to claim 1, wherein said measuring means comprise means for measuring at least one between electric resistance and capacity.

6. Device according to claim 1, wherein it comprises regeneration means, which can be activated in order to remove from said cavities the solid particles therein collected.

7. Device according to claim 1, wherein it is installed inside an exhaust conduit of an internal combustion engine.

8. Use of the device according to claim 1 for detecting the concentration of particulate matter in exhaust gases of an internal combustion engine of a motor vehicle, in particular a diesel engine.

9. Device according to claim 1, wherein said measuring means are operative to detect a variation in the value of the measured quantity with respect to an initial or reference value, and to estimate in an integral way, as a function of said variation, the amount or concentration of solid particles in the gas medium.

10. Device according to claim 9, wherein said regeneration means comprise heating means, which can heat said structure up to a temperature causing removal of the solid particles collected in said cavities.

11. Device according to claim 1, wherein a first end of said cavities overlooks said first electrode, which acts as closing element for said cavities on said first ends.

12. Device according to claim 11, wherein said first electrode is at least partly made of aluminum.

13. Device according to claim 1, wherein said porous body is placed between the first and second electrode.

14. Device according to claim 13, wherein at least one layer of electrically insulating material is placed between said second electrode and said porous body.

15. Device according to claim 14, wherein said second electrode and said insulating layer are shaped like a grid.

16. Device for detecting the amount or concentration of solid particles of nanometric or sub-micrometric size in a gas medium, in particular particulate matter in the exhaust gas of an internal combustion engine, comprising:

a structure for the deposit of solid particles present in the gas medium, at least a first and a second electrode associated to said structure, and means for measuring an electric quantity between the first and second electrode, wherein a plurality of cavities is defined in said structure, which act as collectors of solid particles present in the gas medium, the structure being arranged so as to enable collection of said particles inside said cavities, and wherein a first end of said cavities overlooks said first electrode, which acts as a closing element for said cavities on said first ends.

17. Device for detecting the amount or concentration of solid particles of nanometric or sub-micrometric size in a gas medium, in particular particulate matter in the exhaust gas of an internal combustion engine, comprising:

a structure for the deposit of solid particles present in the gas medium, at least a first and a second electrode associated to said structure, and means for measuring an electric quantity between the first and second electrode, wherein a plurality of cavities is defined in said structure, which act as collectors of solid particles present in the gas medium, the structure being arranged so as to enable collection of said particles inside said cavities, and wherein said measuring means are operative to detect a variation in the value of the measured quantity with respect to an initial or reference value, and to estimate in an integral way, as a function of said variation, the amount or concentration of solid particles in the gas medium.

18. Particulate matter sensor device for cumulative integral measuring of an amount or concentration of solid particles in a gas medium, the sensor device comprising:

a structure for a deposit of submicrometric or nanometric solid particles of particulate matter present in the gas medium, at least a first and a second electrode associated to said structure, and means for measuring an electric quantity between the first and second electrode, wherein a plurality of cavities is defined in said structure, which act as collectors of said solid particles, the structure being arranged so as to enable collection of said solid particles inside said cavities, wherein said structure comprises a porous body made of an electrically insulating material, the porous body having through pores constituting at least part of said cavities, said pores having a first end and a second end, said porous body is arranged between said electrodes such that said first electrode closes said pores at the first ends thereof and said second electrode does not obstruct said pores at the second ends thereof, the sensor device is designed to be arranged within a conduit in which a flow of said gas medium flows in a flow direction, with the second ends of said pores being opposed to said flow direction such that said solid particles can enter said pores and progressively accumulate therein in presence of the flow of the gas, and wherein said measuring means are arranged for:

measuring an initial value of said electrical quantity, detecting a variation of the electrical quantity with respect to said initial value, due to accumulation of said solid particles in said pores caused by said flow of the gas, and estimating in an integral way, as a function of said variation of the electrical quantity, the amount or concentration of said solid particles in the gas medium.

19. Device according to claim 18, wherein said porous body is made at least partly of anodized porous alumina.

20. Device according to claim 18, further comprising regeneration means, which can be activated in order to remove from said pores the solid particles collected therein.

* * * * *